(12) United States Patent
Chen et al.

(10) Patent No.: US 10,150,803 B2
(45) Date of Patent: Dec. 11, 2018

(54) METHOD OF PREPARING GLUCAGON-LIKE PEPTIDE-2 (GLP-2) ANALOG

(71) Applicant: Chunghwa Chemical Synthesis & Biotech Co. Ltd., New Taipei (TW)

(72) Inventors: Shih-Lin Chen, New Taipei (TW); Ting-Yu Hsiung, New Taipei (TW)

(73) Assignee: CHUNGHWA CHEMICAL SYNTHESIS & BIOTECH CO. LTD, New Taipei (TW)

( * ) Notice: Subject to any disclaimer, the term of this patent is extended or adjusted under 35 U.S.C. 154(b) by 48 days.

(21) Appl. No.: 15/407,883

(22) Filed: Jan. 17, 2017

(65) Prior Publication Data

US 2018/0118800 A1    May 3, 2018

(30) Foreign Application Priority Data

Oct. 27, 2016 (TW) .............. 105134783 A

(51) Int. Cl.
- C07K 14/47 (2006.01)
- C07K 14/605 (2006.01)
- C12P 21/02 (2006.01)

(52) U.S. Cl.
CPC ........ C07K 14/605 (2013.01); C07K 14/4702 (2013.01); C12P 21/02 (2013.01); C07K 2319/21 (2013.01)

(58) Field of Classification Search
CPC ......... C07K 14/47; C07K 14/395; C12N 9/52
See application file for complete search history.

(56) References Cited

U.S. PATENT DOCUMENTS

| | | | |
|---|---|---|---|
| 5,789,379 A | 8/1998 | Drucker et al. | |
| 6,872,551 B2 * | 3/2005 | Lima | C12N 15/62 424/94.63 |
| 7,056,886 B2 | 6/2006 | Isaacs | |
| 7,781,567 B2 | 8/2010 | Wagner et al. | |
| 7,829,307 B2 | 11/2010 | Sasaki et al. | |
| 7,847,061 B2 | 12/2010 | Sanguinetti et al. | |

FOREIGN PATENT DOCUMENTS

EP      1 704 234 B1    1/2012

OTHER PUBLICATIONS

Gallwitz et al. 2012; The extended cleavage specificity of human thrombin. PLos One. 7(2): e31756.*
Yan et al. 2009; The use of SUMO as a fusion system for protein expression and purification. Chemistry Today 27(6): 42-47.*
H. Michael Petrassi, et al., "A strategy to profile prime and non-prime proteolytic substrate specificity", Bioorganic & Medicinal Chemistry Letters 15 (2005), 3162-3166.

* cited by examiner

Primary Examiner — Karen Cochrane Carlson
(74) Attorney, Agent, or Firm — Muncy, Geissler, Olds & Lowe, P.C.

(57) ABSTRACT

The present invention relates a method of preparing a Glucagon-like peptide 2 (GLP-2) analog by gene recombination. The present invention provides an expression vector, which includes: (a) a nucleic acid sequence encoding tag protein; (b) a nucleic acid sequence encoding Smt3 protein (SEQ ID NO: 1); and (c) a nucleic acid sequence encoding linker peptide (SEQ ID NO: 2) and GLP-2 analog. The fusion protein expressed by the expression vector can be cleaved by thrombin, wherein the cleaving position is at the linker peptide, and then the GLP-2 analog is produced.

5 Claims, 9 Drawing Sheets

Specification includes a Sequence Listing.

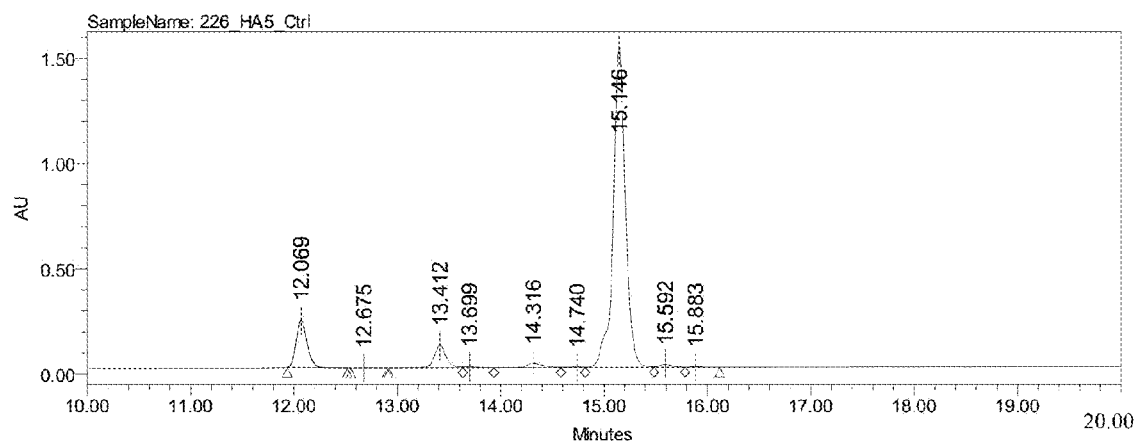
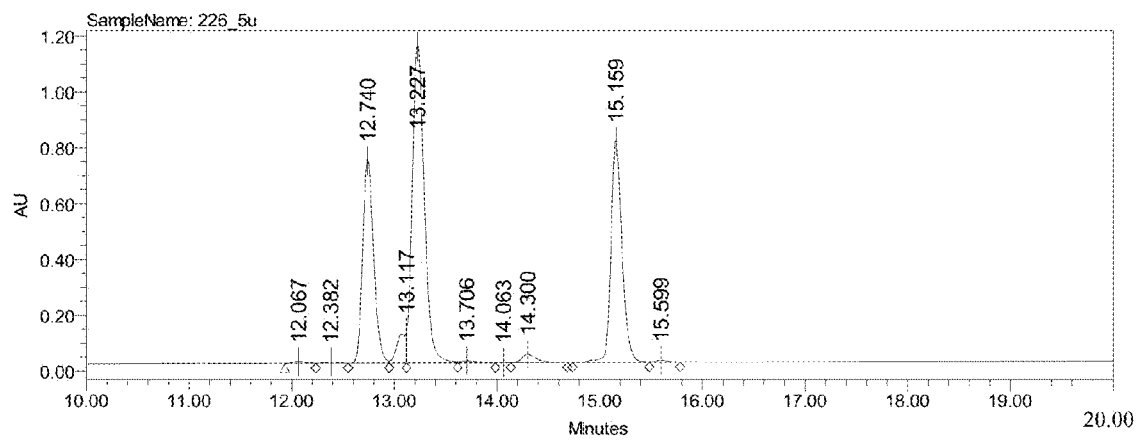
Figure 1

12mer
PVSGPHGDGSF
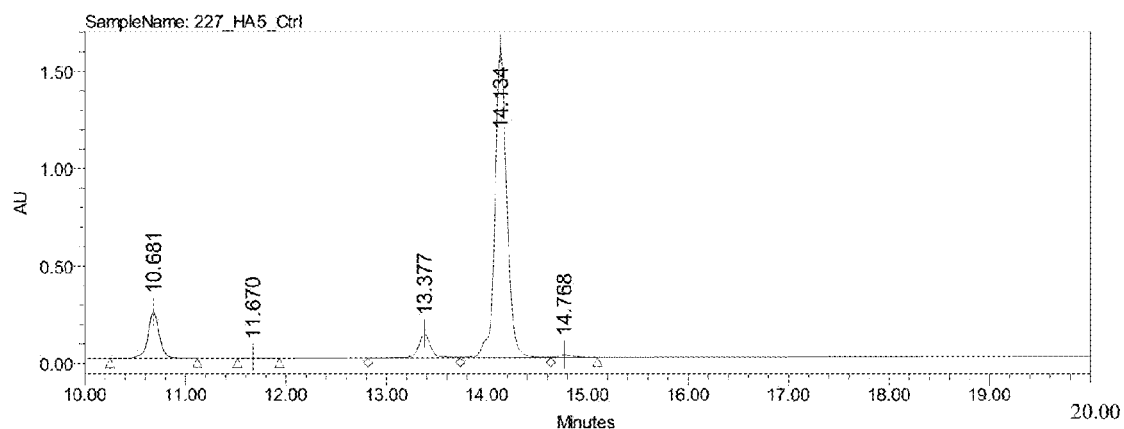
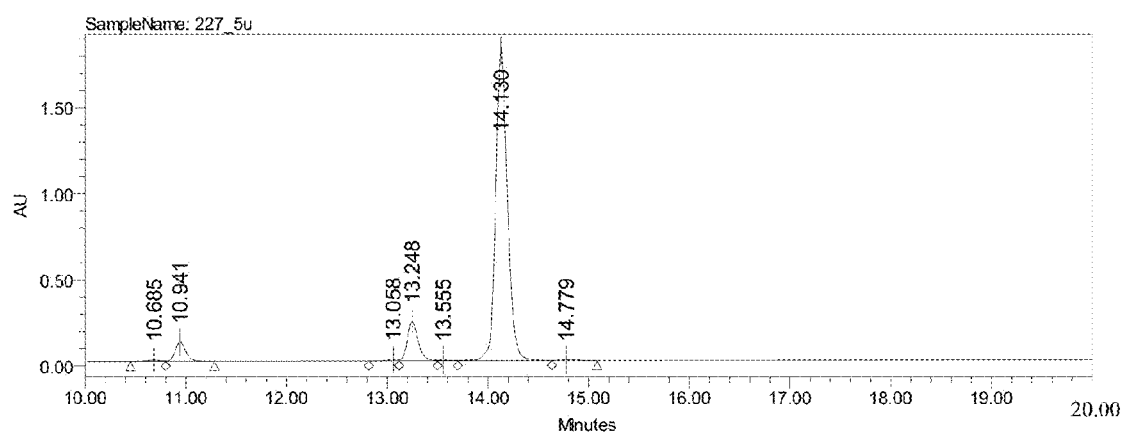
Figure 1(a)

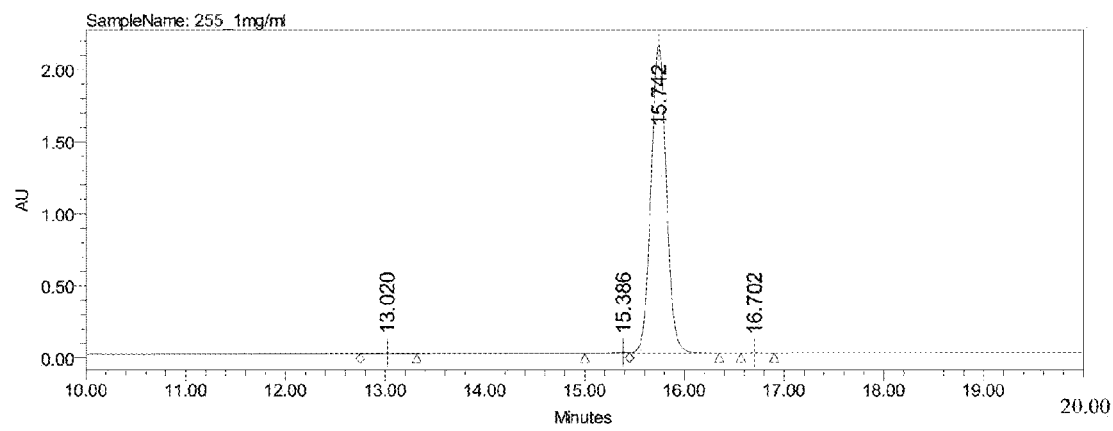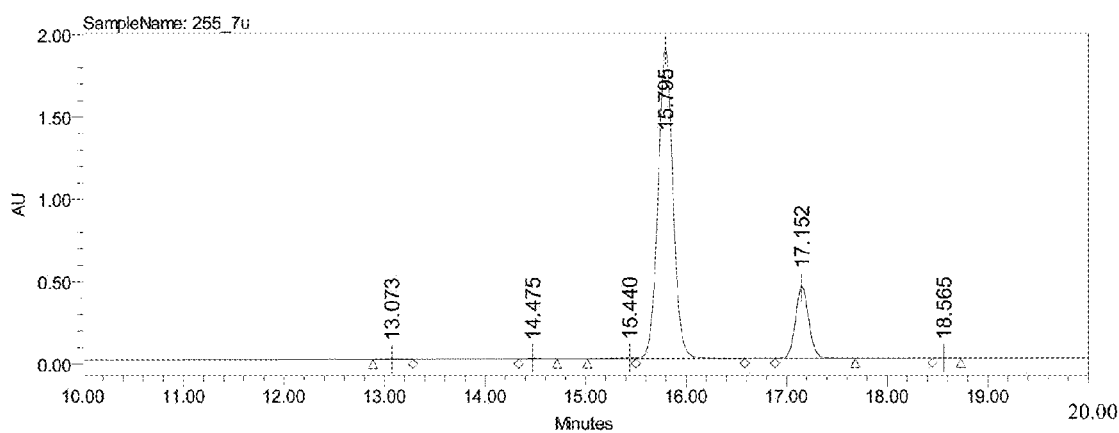
Figure 1(b)

METHOD OF PREPARING GLUCAGON-LIKE PEPTIDE-2 (GLP-2) ANALOG

BACKGROUND OF THE INVENTION

1. Technical Field

The present invention relates to the field of genetic engineering, more particularly to peptide preparation, and even more particularly to a method of preparing a glucagon-like peptide-2 (GLP-2) analog by gene recombination.

2. Description of Related Art

GLP-2 is a peptide consisting of 33 amino acids and has a molecular weight of 3900 Da. It is a product expressed by the proglucagon (PG) gene and is one of the products of proglucagon degradation by prohormone convertase (PC). The amino acid sequence of GLP-2 is highly conservative in mammals. GLP-2 can promote the growth of intestinal mucosa and accelerate regeneration and repair of damaged intestinal mucosa without affecting the multiplication of cells, or the morphological changes of tissues, in other tissues and organs and therefore has great value in the research and development of drugs intended to protect the intestinal tract. GLP-2 has a biological half-life of about 7 minutes in the human circulatory system and is metabolized mainly through renal excretion and by the dipeptidyl peptidase-4 (DPP-4) on the brush borders of the intestinal tract, wherein DPP-4 hydrolyzes the two residues at the amino terminus of GLP-2 to form inactive GLP-2(3-33).

Teduglutide is a GLP-2 analog that is resistant to DPP-4. It is different from GLP-2 only in that its second alanine is substituted by glycine (A2G). Teduglutide can effectively reduce degradation by DPP-4 and hence has an extended biological half-life of about 2 hours in the human circulatory system. A teduglutide-based product developed by NPS Pharmaceuticals of the USA and indicated for gastrointestinal disorders, mainly the short bowel syndrome (SBS), is disclosed in U.S. Pat. Nos. 5,789,379; 7,056,886; and 7,847,061 and has been commercially available in the European Union and the USA since 2012 under the product names Revestive and Gattex respectively. Teduglutide also has significant therapeutic effects on ulcerative colitis as well as on intestinal mucosa damage by chemotherapy intended for cancer.

Teduglutide, however, is very expensive and unaffordable, to patients in general, and in view of this, brand-name drug manufacturers have developed different production processes to increase the yield. For example, U.S. Pat. Nos. 7,781,567 and 7,829,307 and EU Patent No. 1,704,234 disclose increasing the yield of a GLP-2 analog by gene recombination to enhance product competiveness. U.S. Pat. No. 7,781,567, in particular, discloses that a natural GLP-2 analog peptide can be produced by enzymatic cleavage using clostripain, the price of which enzyme is nevertheless too high to be cost efficient and therefore imposes limitations on the production process.

One of the basic requirements of a protein- or peptide-based drug for clinical use is that the amino acid sequence of the protein or peptide must be identical to that of a natural one. Otherwise it must be proved, typically by an exceedingly time-consuming and laborious process, that the additional amino acid(s) or incomplete nucleic acid sequence is harmless to the human body and unconducive to immune rejection. Moreover, if a peptide is to be synthesized, the equipment and technology required will be costly; if a peptide is to be expressed by gene recombination, its molecular weight tends to be so low that purification becomes difficult.

Fusion protein technology, i.e., expressing in a host cell a target protein fused with a protein partner, allows for enhanced expression of the target protein, which is protected from degradation/mis-folding, easy to be purified/detected, and has improved solubility. The protein partner usually would interfere with the structural or functional properties of the target protein and therefore needs to be removed via, e.g., chemical or enzymatical cleavage, from a fusion protein to generate a free target protein. Cleavage of the protein partner remains the major disadvantage in conventional fusion technology as imprecise cleavage, which occurs frequently, results in failure to recover an active or structurally intact target protein. In addition, the restriction of limited types, high price, and low hydrolysis efficiency of the cleaving enzymes causes disadvantages to the production process by fusion protein technology. Small-ubiquitin-related modifier (SUMO) fusion protein technology is a technique for increasing the solubility of fusion protein. SUMO protease can recognize the quaternary structure of SUMO protein instead of peptides sequence, and precisely remove the SUMO protein to produce a native target protein. However, due to the expensive price and great variance of hydrolysis efficiency between different matrices of SUMO protease, the extension of production process is still limited. [Non-patent literature] Petrassi et al., Bioorganic & Medicinal Chemistry Letters 15:3162-3166 (2005).

BRIEF SUMMARY OF THE INVENTION

The inventor of the present invention found that, based on the production processes disclosed in U.S. Pat. No. 7,829,307 and EP Patent No. 1,704,234, a peptide multimer with seven series-connected GLP-2 analog units can produce GLP-2 analog peptide segments of the size 4K when subjected to an acidic treatment, and that multimers of higher molecular weights, however, are also produced. As the number of 4K peptide segments reduces while the acid treatment continues, a significant variation between batches will result. In addition, although peptide segments of certain fixed types are produced when the former multimer is treated, or more specifically cleaved, with thrombin, the number of 4 k peptide segments is still limited. These findings show that the production processes of the aforecited patents may present difficulties when executed; in other words, a practical method for preparing a GLP-2 analog peptide by recombination of nucleic acid sequences has yet to be developed.

After studying the document of Petrassi et al. (2005) and the disclosure of U.S. Pat. No. 7,629,437, the inventor found that the foregoing drawbacks of the prior art can be overcome with the newly developed fusion protein technology, which entails the use of a small ubiquitin-like modifier (SUMO) and a linker. Accordingly, the present invention provides a modified fusion protein system that employs a SUMO and a linker to enable directional multiplication of any target gene and hence rapid purification of a natural target protein or peptide.

When cleaved with thrombin, the N-terminus, where the target peptide resides, tends to be left with two amino acids (Gly-Ser), making it impossible to produce a peptide that is identical to a natural one. In the present invention, therefore, the expression vector is prepared by polymerase chain reactions (PCR) and by cleaving particular nucleic acid sequences with restriction enzymes such that the fusion protein of the expression vector has the nucleic acid sequence of a highly specific linker peptide. This allows the cleavage enzyme to precisely identify, and cleave at, the linker peptide nucleic acid sequence to produce a protein or peptide that is identical to a natural one.

The major objective of the present invention is to provide an expression vector that sequentially includes: (a) a nucleic acid sequence encoding a tag protein; (b) a nucleic acid sequence encoding a Smt3 protein (SEQ ID NO: 1); and (c) a nucleic acid sequence encoding a linker peptide (SEQ ID NO: 2) and a target protein. The expression vector can be introduced into a host cell to express a fusion protein that includes, from the N-terminus to the C-terminus, the tag protein, the Smt3 protein, the linker peptide, and the target protein. The C-terminus, where the linker peptide resides, is subsequently cleaved with thrombin to produce a natural target protein.

Another object of the present invention is to provide a method of preparing a glucagon-like peptide 2 (GLP-2) analog, wherein the steps of the method includes: (i) preparing the aforementioned expression vector of the present invention, wherein the target protein is a GLP-2 analog; (ii) introducing the prepared expression vector into a host cell to express a fusion protein that includes, from the N-terminus to the C-terminus, the tag protein, the Smt3 protein, the linker peptide, and the GLP-2 analog; (iii) cleaving the C-terminus of the linker peptide of the fusion protein by a protease for cleaving fusion protein and thereby producing a GLP-2 analog.

BRIEF DESCRIPTION OF THE SEVERAL VIEWS OF THE DRAWINGS

FIG. 1 displays three sets of chromatograms, showing the analysis results of products obtained by cleaving three peptides (namely PLTPRHGDGSF (SEQ ID NO: 6), PVS-GPRHGDGSF (SEQ ID NO: 7), and ITDPLVPRHGDGS (SEQ ID NO: 8)) with thrombin respectively, wherein the analysis was performed by column chromatography (RP-HPLC, C 18 column), and wherein the upper chromatogram of each set represents one of the original peptides synthesized while the lower chromatogram represents the product obtained by cleaving the peptide;

FIG. 2 shows how a His6-Smt3-Linker-GLP-2 analog expression vector is prepared according to the present invention;

DETAILED DESCRIPTION OF THE INVENTION

Figure 3:
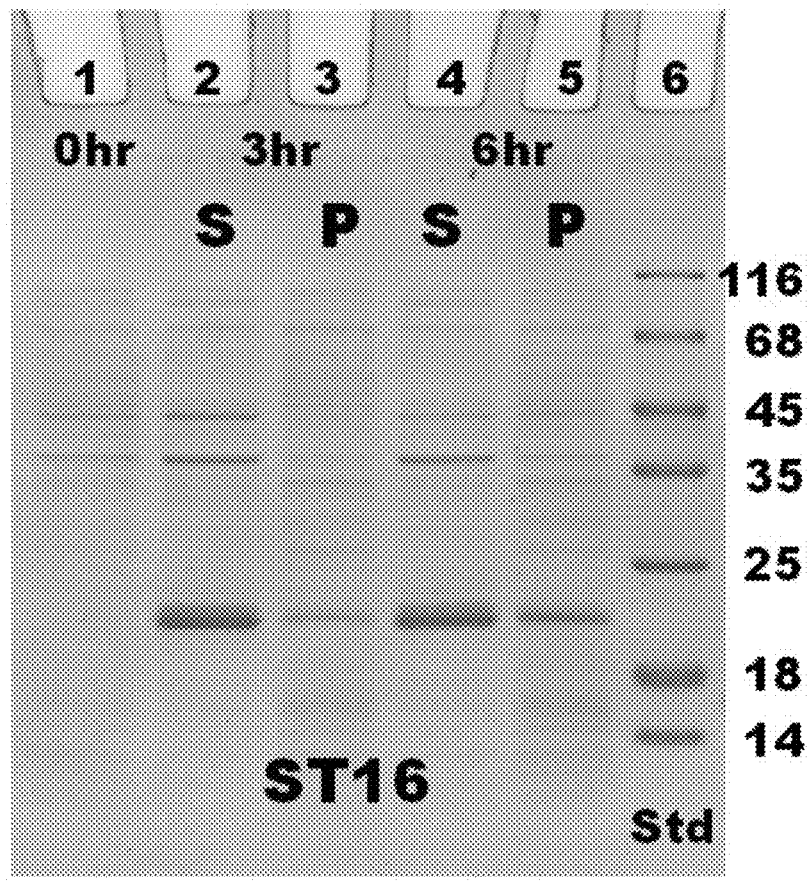
FIG. 3 shows the analysis results of the His6-Smt3-Linker-GLP-2 analog fusion protein in embodiment 2, wherein the analysis was performed by sodium dodecyl sulfate polyacrylamide gel electrophoresis (SDS-PAGE)

The following detailed description is the implement of the aforementioned expression vector, method of preparing a native protein, and method of preparing method of preparing a glucagon-like peptide 2 (GLP-2) analog of the present invention.

In the present invention, a "SUMO (small ubiquitin-related modifier) protein" refers to a protein that is but not limited to Smt3 protein from *Saccaromyces cerevisiae*. For example, a Smt3 protein can be SEQ ID NO:1 and the amino acid sequence of SEQ ID NO:3, or the functional variant of the yeast Smt3 protein, which is a polypeptide that has high similarity of nucleic acid sequence with Smt3 protein (a polypeptide with at least 85%, 90%, 95%, or 99% nucleic acid sequence similarity). When nucleic acid sequence encoding the functional variant of the yeast Smt3 protein links a tag protein, such as hexa histidine (His6), with the linker peptide and the target protein to form an expression vector, the expression vector can be introduced into a host cell to express a fusion protein. After that, the C-terminus of the linker peptide of the fusion protein can be cleaved by the thrombin to remove the functional variant of the yeast Smt3 protein, tag protein, and linker peptide, and then produce a native target peptide.

In the present invention, a "tag protein" refers to a protein that is used in a fusion protein system in the following manner. When purifying a fusion protein, an affinity column capable of forming a reversible bond with the molecule of a certain tag protein may be used so that only a fusion protein containing the tag protein is adsorbed to the affinity column whereas all the unadsorbed proteins and impurities are washed out. The desired fusion protein is then obtained by purifying it with a suitable buffer. The tag protein in the present invention includes but is not limited to hexa histidine (His6), maltose-binding protein, the N-utilizing substance A, thioredoxin, calmodulin-binding protein, glutathione S-transferase, and the α-factor. His6 is preferably used as the tag protein.

In the present invention, a "linker" is a peptide segment, and the site where a linker is located on a fusion protein can be specifically cleaved by a chemical or enzymatic means. The more vulnerable to attack such a site is, the higher the cleaving efficiency will be, and the more the free-state target peptide obtained by cleaving. In the present invention, SEQ ID NO: 2 is the amino acid sequence of linker peptide.

In the present invention, a "target protein" refers to the free- or fused-state protein or peptide to be produced. The preferred target protein in the present invention is a natural target GLP-2 analog peptide (SEQ ID NO: 9). Moreover, in the embodiments of the present invention that are disclosed herein, the nucleic acid encoding linker peptide (SEQ ID NO: 2) and the nucleic acid sequence of SEQ ID NO: 10 encoding the target protein of SEQ ID NO: 9 are on the same nucleic acid sequence prepared by a polymerase chain reaction (PCR). In a more preferable embodiment, a pair of primers of SEQ ID NO: 4 and SEQ ID NO: 5 are used in the PCR as a forward primer and a reverse primer respectively.

In the present invention, the protease used to cleave a fusion protein is preferably "thrombin", which is a serine protease capable for catalyzing various blood coagulation-related reactions. In a genetic engineering expression system, a fusion protein can be treated with thrombin to separate the peptide segments of a partner protein (e.g., the linker peptide in the present invention) in the fusion protein from those of a target protein, and the most appropriate cleavage site can be expressed as: P4-P3-P2-Arg↓-P1'-P2', where P4 and P3 are hydrophobic amino acids, P1' and P2' are non-acid amino acids, and ↓ is the cleavage site; that is to say, two residues remain at the N-terminus of the cleaved protein. The present invention, by contrast, uses a specially designed linker to solve the problem of extra residues after cleavage.

In the present invention, an "expression vector" is a plasmid containing a high-performance promotor and one or more cloning sites downstream the promoter. This plasmid is introduced into a host cell, where the plasmid expresses the target protein nucleic acid sequence inserted at one of the cloning sites. By cloning a target protein nucleic acid sequence into an expression vector, an expression construct vector is generated.

EMBODIMENTS

The following description is the essential techniques of the present invention that can be understood by the person having ordinary skill in the art. And without inconsistence of the scope or spirits of the present invention, the changes and modification can be done for different condition and application. Thus, the implement with changes and modification of the present invention still fall within the claims of the present invention.

Test Example: Cleaving the Amino Acid Sequence of a Linker Peptide with Thrombin Three peptides, namely PLTPRHGDGSF (SEQ ID NO: 6), PVSGPRHGDGSF (SEQ ID NO: 7), and ITDP LVPRHGDGS (SEQ ID NO: 8), were synthesized separately, wherein the double-underlined amino acid sequences were intended as the linker peptide sequences while the peptide sequences at the rear ends served as the starting amino acids of the amino acid sequence (SEQ ID NO: 9) of a teduglutide (i.e., a GLP-2 analog). Each of the three peptides was cleaved with thrombin, and the cleaved products were tested by column chromatography (RP-HPLC, C18 column). The analysis results of the three peptides before and after thrombin cleavage are shown in FIG. 1 (in which the upper chromatograms correspond respectively to the original peptides not yet cleaved with thrombin, the lower chromatograms correspond respectively to the products of thrombin cleavage, and the arrows indicate the peptide segment HGDGSF (amino acids 6-11 of SEQ ID NO: 6) or HGDGS (amino acids 9-13 of SEQ ID NO: 8)). As can be seen in FIG. 1, PLTPRHGDGSF (SEQ ID NO: 6) was cleaved the most thoroughly. This means that the highest cleavage efficiency was achieved by choosing the LTPR (SEQ ID NO: 2) sequence as the linker peptide when cleaving with thrombin.

Embodiment 1: His6-Smt3-LTPR-GLP-2 Analog Expression Vector

Please refer to FIG. 2.

(a) A nucleic acid sequence containing a nucleic acid sequence encoding the tag protein His6 and a nucleic acid sequence encoding the Smt3 protein of distillers' yeast were prepared by PCR, treated with purified and replicated NdeI and BamHI restriction enzymes for deoxyribonucleic acids, and then cloned into a pET30 expression vector (Novagen, USA) to form a His-Smt3 expression vector, as shown in part (a) of FIG. 2.

(b) A nucleic acid sequence encoding the LTPR linker peptide (LTPR) and GLP-2 analog were prepared by PCR, as shown in part (b) of FIG. 2, using a template sequence as set forth in SEQ ID NO: 10 and primers as set forth in SEQ ID NOS: 4 and 5.

(c) The His6-Smt3 expression vector in (a) and the nucleic acid sequence encoding LTPR and GLP-2 analog in (b) were treated with the BamHI and EcoRI restriction enzymes in order to clone the nucleic acid sequence encoding LTPR and the GLP-2 analog into the pHis6-Smt3 expression vector, thereby forming a His6-Smt3-LTPR-GLP-2 analog expression vector, as shown in part (c) of FIG. 2.

Embodiment 2: His6-Smt3-LTPR-GLP-2 Analog Fusion Protein

The His6-Smt3-LTPR-GLP-2 analog expression vector obtained from embodiment 1 was subjected to DNA sequencing and was confirmed to be a His6-Smt3-LTPR-GLP-2 analog expression vector with the correct nucleic acid sequence. The His6-Smt3-LTPR-GLP-2 analog expression vector was transformed into a BL21(DE3)-competent cell (*Escherichia coli*), and a GLP-2 analog-containing transformed strain, named ST16, was then screened out from an LB (Luria-Bertani) agar medium containing 50 mg/L of kanamycin and was cultivated in an LB nutrient broth containing 50 mg/L of kanamycin, into which glycerol was subsequently added at 10%, and which was afterward stored in separate tubes in a −70° C. freezer. Remove a 10 µl aliquot from one tube of the ST16 transformed strain was cultivated overnight into 5 ml of fresh LB nutrient broth containing 50 mg/L of kanamycin at 37° C., and a small sample was taken from the tube the next day, added into 100 ml of fresh LB nutrient broth containing 50 mg/L of kanamycin, and cultivated at 37° C. Once the optical density OD 600 reached about 0.7-0.8, 1 mM isopropyl-β-D-1-thiogalactopyranoside (IPTG) was added into the nutrient broth in order to induce expression of the His6-Smt3-LTPR-GLP-2 analog expression vector and consequently production of a His6-Smt3-LTPR-GLP-2 analog fusion protein.

Qualitative Analysis of His6-Smt3-LTPR-GLP-2 Analog Fusion Protein

The *E. coli* transformant cells induced to produce the His6-Smt3-LTPR-GLP-2 analog fusion protein were cultivated at 37° C. for 0 to 6 hours, and bacteria of different stages were collected by centrifugation. The *E. coli* transformant cell clumps collected were dissolved with the B-PER bacterial protein extraction reagent (Thermo Scientific, USA) and divided by centrifugation into a soluble portion (expressed as S) and an insoluble portion (expressed as P); the soluble portion is His6-Smt3-LTPR-GLP-2 analog fusion protein and the insoluble portion is the fragments of the E. coli transformant cells. Sodium dodecyl sulfate polyacrylamide gel electrophoresis (SDS-PAGE) analysis and Coomassie blue staining were then conducted, and several bands were detected, as shown in FIG. 3. The major bands correspond to the His6-Smt3-LTPR-GLP-2 analog fusion protein in the soluble portion.

Purification of His6-Smt3-LTPR-GLP-2 Analog Fusion Protein

The His6-Smt3-LTPR-GLP-2 analog fusion protein was purified with a nickel ion ($Ni^{2+}$) affinity chromatography column. More specifically, a liquid chromatograph (AKTA purifier 100 by GE Healthcare, Sweden) was used in conjunction with a 6-ml Profinity IMAC resin column (Bio-Rad, USA). Besides, a buffer for protein adsorption and for removing unwanted proteins was prepared from 20 mM tris(hydroxymethyl)aminomethane (Tris) and 300 mM NaCl (pH 8.0), and a buffer for eluting the target fusion protein was prepared from 20 mM Tris, 300 mM NaCl, and 500 mM imidazole (pH 8.0) in order to perform gradient elution on the adsorbed His6-Smt3-LTPR-GLP-2 analog fusion protein and thereby obtain a purified His6-Smt3-LTPR-GLP-2 analog fusion protein.

Figure 4:
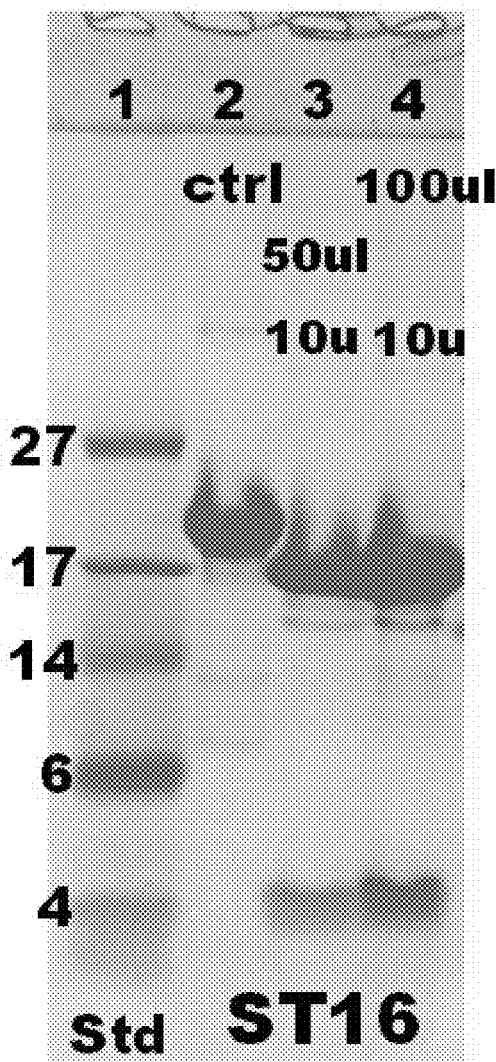
FIG. 4 shows the SDS-PAGE analysis results of the His6-Smt3-Linker-GLP-2 analog fusion protein in embodiment 3 and of the product obtained by cleaving the His6-Smt3-Linker-GLP-2 analog fusion protein with thrombin, wherein the analysis was performed on purified samples.

Embodiment 3: Cleaving His6-Smt3-LTPR-GLP-2 Analog Fusion Protein with Thrombin to Produce GLP-2 Analog Peptide (a) The His6-Smt3-LTPR-GLP-2 analog fusion protein roughly extracted from the E. coli transformant cells in embodiment 2 was added into a column containing $Ni^{2+}$ resin and was washed with the washing buffer prepared in embodiment 2. The His6-Smt3-LTPR-GLP-2 analog fusion protein bound to the $Ni^{2+}$ resin could not be washed out in the beginning but was eluted from the $Ni^{2+}$ resin when 16-30% gradient elution was performed. The Coomassie blue staining results after SDS-PAGE analysis reveal a single band as shown in FIG. 4, demonstrating that the His6-Smt3-LTPR-GLP-2 analog fusion protein obtained was pure to a certain degree. The ultimate yield was 9 mg of fusion protein out of each 100 ml or so of culture medium (nutrient broth).

(b) Furthermore, the His6-Smt3-Linker-GLP-2 analog fusion protein purified with the $Ni^{2+}$ affinity chromatography column was cleaved with thrombin. The two major bands detected through Coomassie blue staining after SDS-PAGE analysis corresponded respectively to His6-Smt3-Linker, whose molecular weight is relatively high, and a GLP-2 analog, whose molecular weight is relatively low, as shown in FIG. 4. This means that thrombin had only one cleavage site on the His6-Smt3-Linker-GLP-2 analog fusion protein.

Comparison Between GLP-2 Analog Peptide and Teduglutide

The N-terminus of the purified GLP-2 analog peptide in embodiment 3 was cleaved by the Edman degradation method to determine the accuracy of the thrombin cleavage site. The test results show that the N-terminus sequence of the GLP-2 analog peptide was identical to that corresponding to its gene. Also, referring to FIG. 7, the mass spectrometer test results show that the molecular weight of the purified GLP-2 analog peptide was about 3,752.12 Da, which is very close to that (3,752.08 Da) of teduglutide.

Comparative Example: Cleaving His6-Smt3-GLP-2 Analog Fusion Protein with Ulp1 Protease to Produce GLP-2 Analog Peptide (a) In the comparative example, Ulp1 protease, which is a SUMO protease, was used for cleaving, and the fusion protein to be cleaved was a His6-Smt3-GLP-2 analog fusion protein, which did not contain the nucleic acid sequence of a linker peptide.

Figure 5:
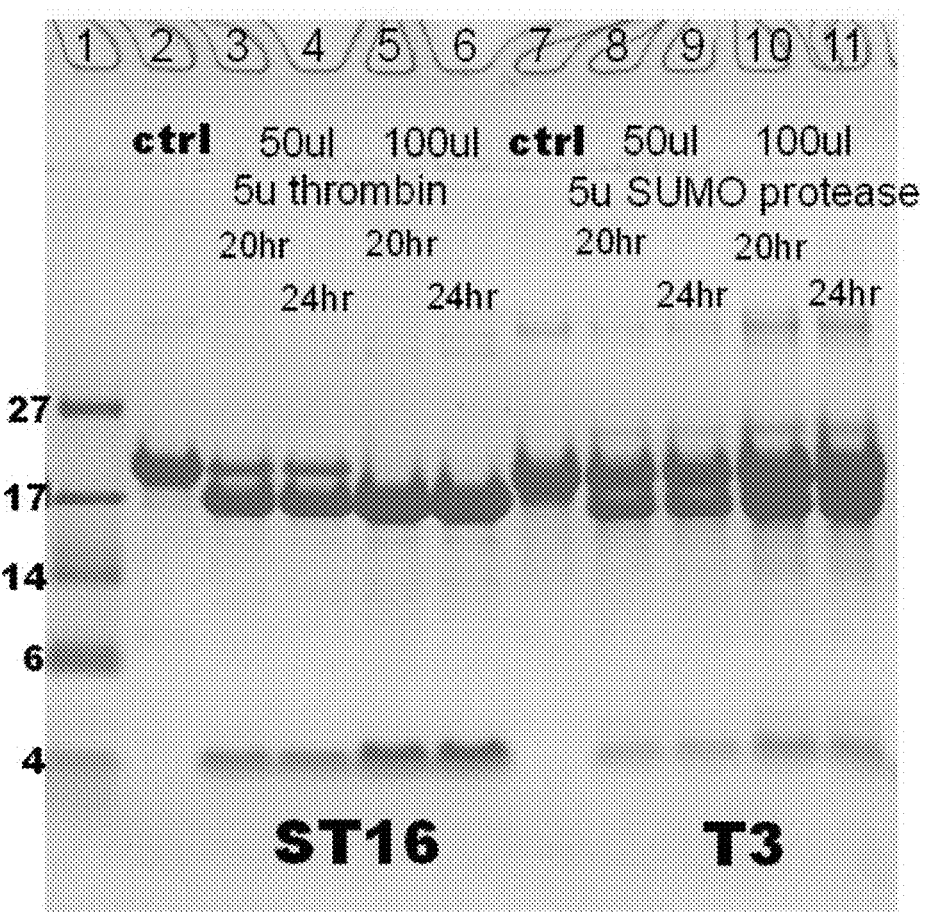
FIG. 5 shows the SDS-PAGE analysis results of the His6-Smt3-Linker-GLP-2 analog fusion protein in embodiment 3, of the product obtained by cleaving the His6-Smt3-Linker-GLP-2 analog fusion protein with thrombin, of the His6-Smt3-GLP-2 analog fusion protein in the comparative example, and of the product obtained by cleaving the His6-Smt3-GLP-2 analog fusion protein with U1p1 protease, wherein the analysis was performed on purified samples.
Figure 7:
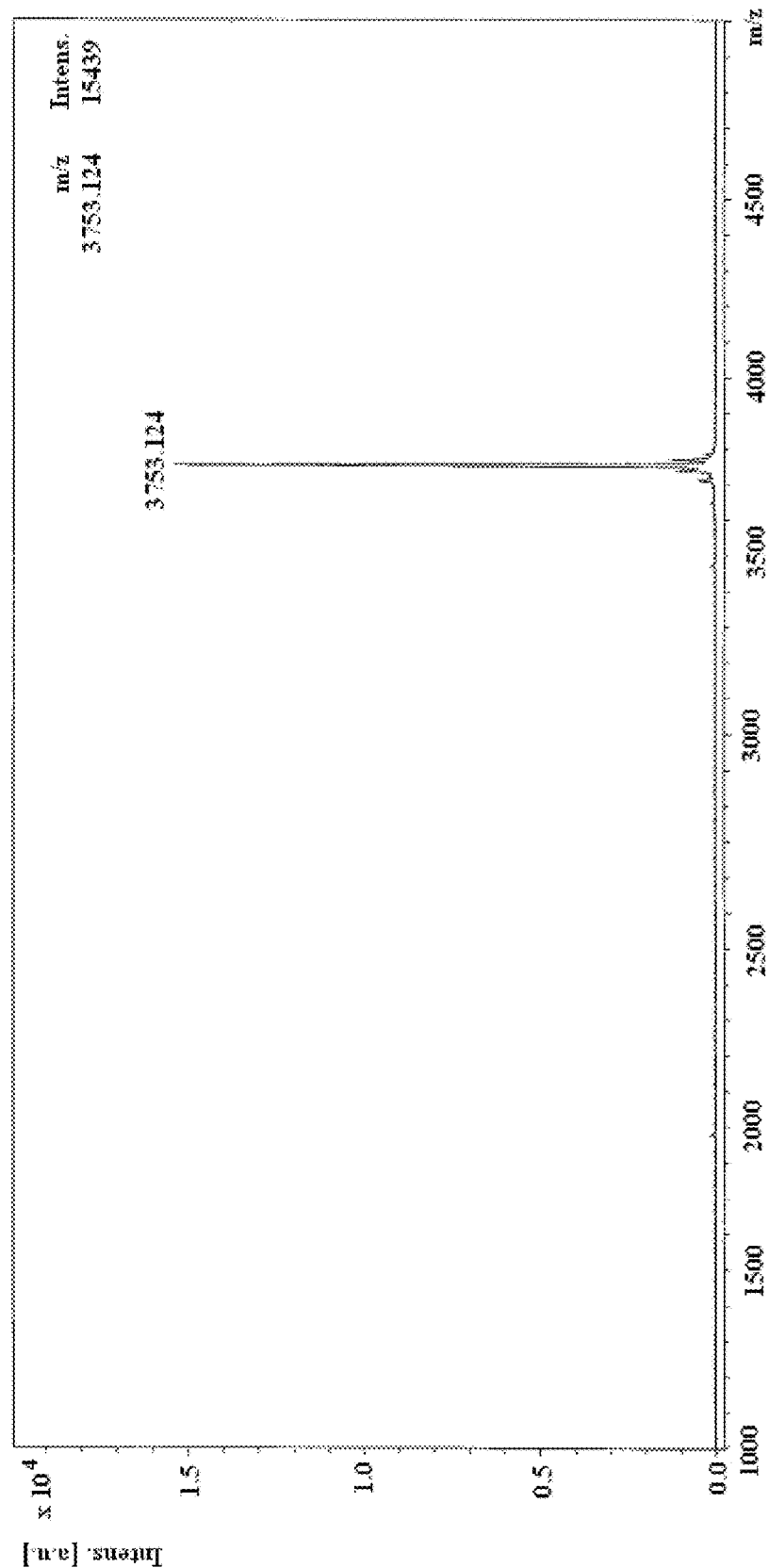
FIG. 7 shows the RP-HPLC analysis results of the product (i.e., GLP-2 analog) of the His6-Smt3-Linker-GLP-2 analog fusion protein in embodiment 3.

(b) The product obtained by cleaving the His6-Smt3-GLP-2 analog fusion protein with Ulp1 protease was purified with a $Ni^{2+}$ affinity chromatography column and was subjected to SDS-PAGE analysis and Coomassie blue staining. The three major bands detected (see the results of sample T3 in FIG. 5) correspond respectively to His6-Smt3-GLP-2, whose molecular weight is the highest, His6-Smt3, whose molecular weight is the second highest, and a GLP-2 analog, whose molecular weight is the lowest. The test results show that Ulp1 protease had only one cleavage cite on the His6-Smt3-GLP-2 analog fusion protein but cleaved far less efficiently than thrombin cleaving a His6-Smt3-Linker-GLP-2 analog fusion protein. A mass spectrometry analysis using R-HPLC produced consistent results, as shown in FIG. 7.

Figure 6A:
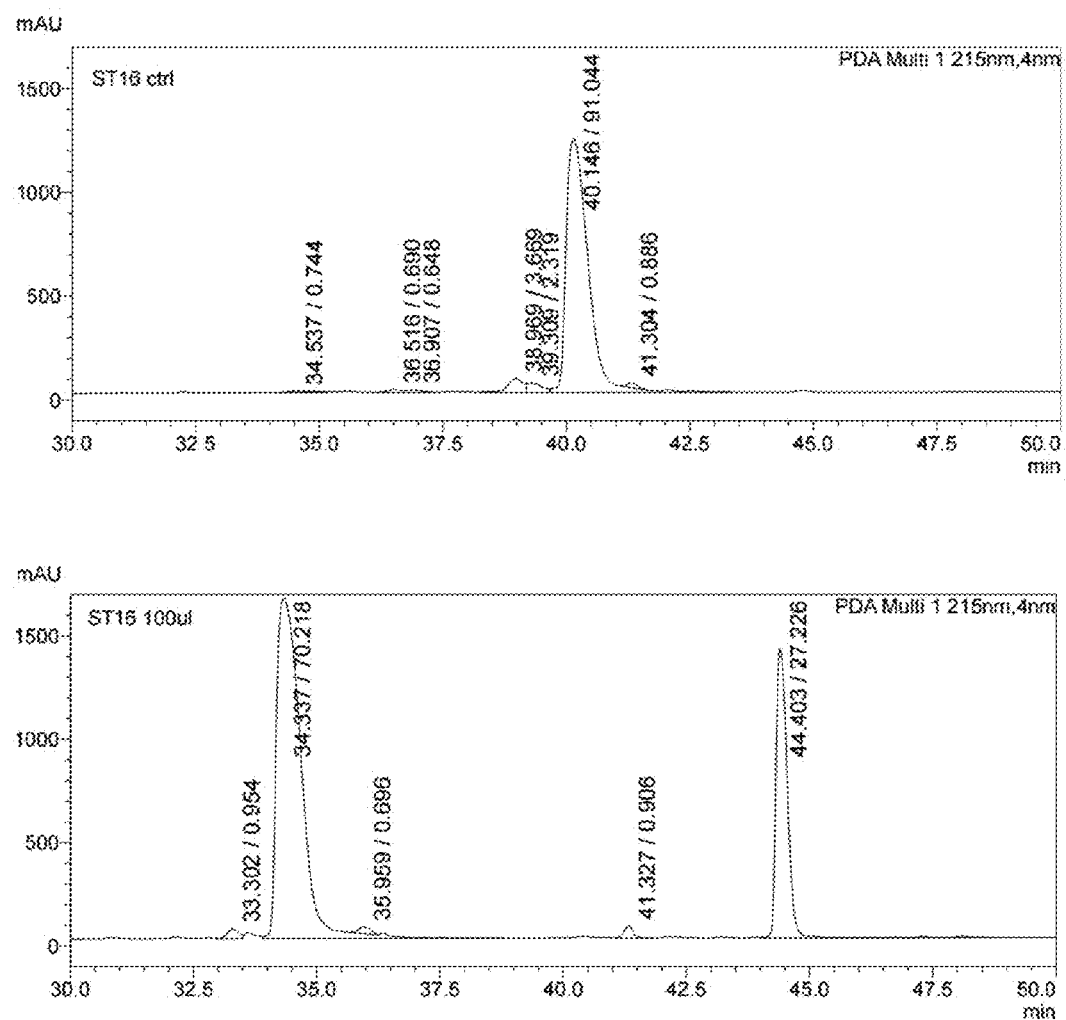
FIGS. 6(a)-6(b) display four chromatograms, showing the analysis results of the His6-Smt3-Linker-GLP-2 analog fusion protein in embodiment 3, of the product obtained by cleaving the His6-Smt3-Linker-GLP-2 analog fusion protein with thrombin, of the His6-Smt3-GLP-2 analog fusion protein in the comparative example, and of the product obtained by cleaving the His6-Smt3-GLP-2 analog fusion protein with U1p1 protease, wherein the analysis was performed by column chromatography (RP-HPLC, C18 column) on purified samples, and wherein each upper chromatogram represents one of the uncleaved fusion proteins while the corresponding lower chromatogram represents the product obtained by cleaving the fusion protein.
Figure 6B:
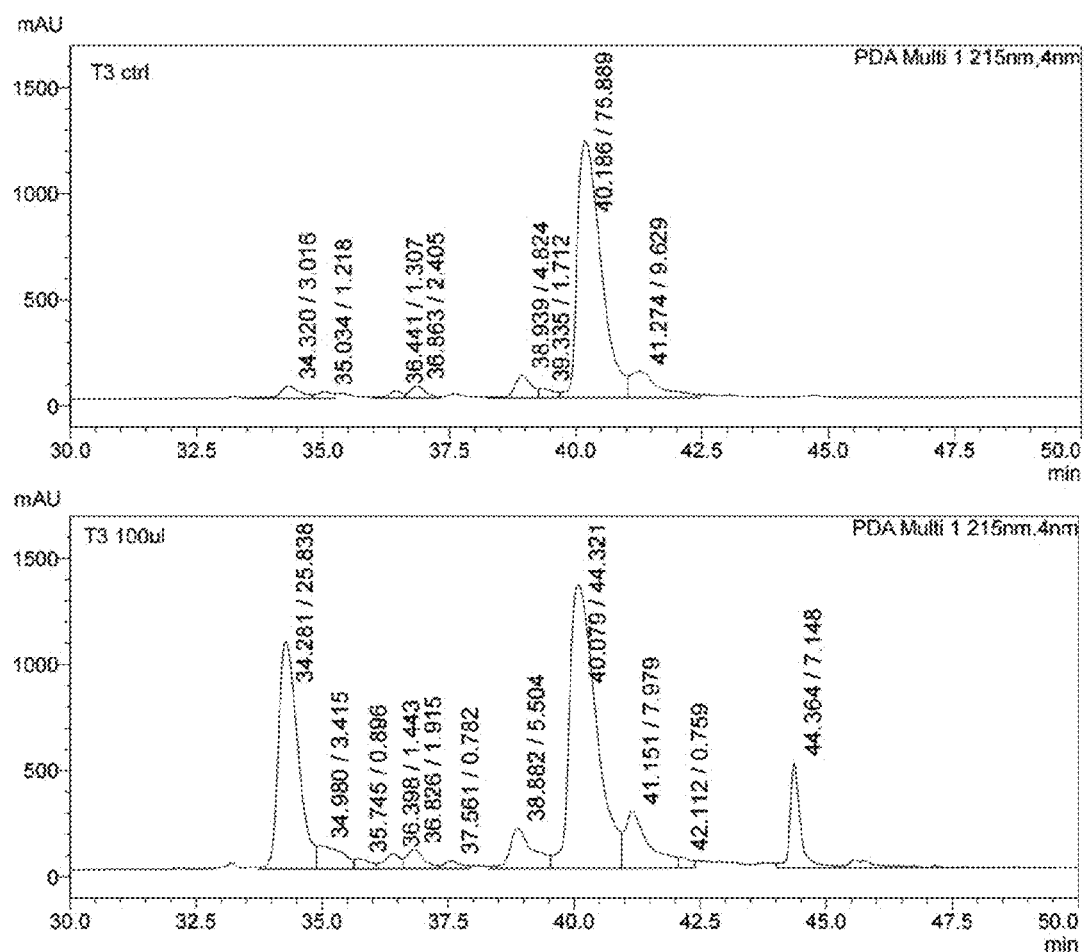

Please refer to FIG. 6, which displays the analysis results performed by RP-HPLC C18 (the upper chromatogram represents one of the uncleaved fusion proteins and the corresponding lower chromatogram represents the product obtained by cleaving the fusion protein). The upper chromatogram of FIG. 6(a) represents His6-Smt3-LTPR-GLP-2 analog fusion protein in embodiment 3; the lower chromatogram of FIG. 6(a) represents the product obtained by cleaving the His6-Smt3-Linker-GLP-2 analog fusion protein with thrombin; the upper chromatogram of FIG. 6(b) represents His6-Smt3-GLP-2 analog fusion protein in comparative example; and, the lower chromatogram of FIG. 6(b) represents the product obtained by cleaving the His6-Smt3-GLP-2 analog fusion protein with Ulp1 protease. It can be known from the results of embodiment 3 that the fusion protein (i.e., His6-Smt3-LTPR-GLP-2 analog fusion protein) expressed by the expression vector in embodiment 3 had a highly specific linker peptide (i.e., the LTPR linker peptide) and produced a complete cleaved product without partially cleaved segments after thrombin cleavage, and that therefore high cleaving efficiency and a high GLP-2 analog yield were achieved. By contrast, the results of the comparative example show that a lack of linker peptide in the His6-Smt3-GLP-2 analog fusion protein gave rise to incomplete cleavage when cleaving was carried out with Ulp1 protease, that uncleaved His6-Smt3-GLP-2 analog fusion protein was found in the product, and that low cleaving efficiency and a low GLP-2 analog yield ensued.

It can be inferred from the above that, because of the nucleic acid sequence of the specific linker peptide, the expression vector of the present invention features a higher yield of its target protein or peptide than the conventional fusion proteins containing a SUMO and a linker, than the conventional methods of preparing a natural target protein with such a fusion protein, and than the gene recombination methods typically used in the prior art to prepare a target protein. The method of the present invention is therefore suitable for producing a natural protein or peptide in large quantities.

What is claimed is:

1. An expression vector, which sequentially includes:
   (a) a nucleic acid sequence encoding a tag protein;
   (b) a nucleic acid sequence encoding a Smt3 protein of SEQ ID NO: 1; and
   (c) a nucleic acid sequence encoding a linker peptide of SEQ ID NO: 2 and a target protein of Teduglutide.

2. The expression vector of claim 1, wherein the tag protein is selected from hexa histidine (His6), maltose-binding protein, N-utilizing substance A, thioredoxin, calmodulin-binding protein, glutathione S-transferase, and α-factor.

3. The expression vector of claim 2, wherein the tag protein is hexa histidine (His6).

4. A host cell, comprising the expression vector of claim 1.

5. A method of preparing a glucagon-like peptide 2 (GLP-2) analog, wherein the method includes the following steps:
   (i) preparing the expression vector of claim 1;
   (ii) introducing the prepared expression vector into a host cell to express a fusion protein that includes, from the N-terminus to the C-terminus, the tag protein, the Smt3 protein, the linker peptide, and the teduglutide; and
   (iii) cleaving the C-terminus of the linker peptide of the fusion protein with thrombin and thereby producing teduglutide.

* * * * *

SEQUENCE LISTING

<160> NUMBER OF SEQ ID NOS: 10

<210> SEQ ID NO 1
<211> LENGTH: 98
<212> TYPE: PRT
<213> ORGANISM: Unknown
<220> FEATURE:
<223> OTHER INFORMATION: Smt3 amino acid
<220> FEATURE:
<221> NAME/KEY: PEPTIDE
<222> LOCATION: (1)..(98)

<400> SEQUENCE: 1

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly

<210> SEQ ID NO 2
<211> LENGTH: 4
<212> TYPE: PRT
<213> ORGANISM: Unknown
<220> FEATURE:
<223> OTHER INFORMATION: linker
<220> FEATURE:
<221> NAME/KEY: UNSURE
<222> LOCATION: (1)..(4)

<400> SEQUENCE: 2

Leu Thr Pro Arg
1

<210> SEQ ID NO 3
<211> LENGTH: 111
<212> TYPE: PRT
<213> ORGANISM: Unknown
<220> FEATURE:
<223> OTHER INFORMATION: tag protein fused with Smt3
<220> FEATURE:
<221> NAME/KEY: PEPTIDE
<222> LOCATION: (1)..(111)

<400> SEQUENCE: 3

Met Gly Ser His His His His His Gly Ser Leu Ser Asp Ser Glu
1               5                   10                  15

Val Asn Gln Glu Ala Lys Pro Glu Val Lys Pro Glu Val Lys Pro Glu
            20                  25                  30

Thr His Ile Asn Leu Lys Val Ser Asp Gly Ser Ser Glu Ile Phe Phe
        35                  40                  45

Lys Ile Lys Lys Thr Thr Pro Leu Arg Arg Leu Met Glu Ala Phe Ala
    50                  55                  60

Lys Arg Gln Gly Lys Glu Met Asp Ser Leu Arg Phe Leu Tyr Asp Gly
65                  70                  75                  80

Ile Arg Ile Gln Ala Asp Gln Thr Pro Glu Asp Leu Asp Met Glu Asp
                85                  90                  95

Asn Asp Ile Ile Glu Ala His Arg Glu Gln Ile Gly Gly Gly Ser
            100                 105                 110

<210> SEQ ID NO 4
<211> LENGTH: 36
<212> TYPE: DNA
<213> ORGANISM: Unknown
<220> FEATURE:
<223> OTHER INFORMATION: Ted-forward primer
<220> FEATURE:
<221> NAME/KEY: primer_bind
<222> LOCATION: (1)..(36)

<400> SEQUENCE: 4
tcaggatccc tgaccccacg tcatggtgat ggtagc                               36

<210> SEQ ID NO 5
<211> LENGTH: 29
<212> TYPE: DNA
<213> ORGANISM: Unknown
<220> FEATURE:
<223> OTHER INFORMATION: Ted-reverse primer
<220> FEATURE:
<221> NAME/KEY: primer_bind
<222> LOCATION: (1)..(29)

<400> SEQUENCE: 5
agtgaattct tatcagtcgg tgattttgg                                      29

<210> SEQ ID NO 6
<211> LENGTH: 11
<212> TYPE: PRT
<213> ORGANISM: Unknown
<220> FEATURE:
<223> OTHER INFORMATION: testing peptide 1
<220> FEATURE:
<221> NAME/KEY: PEPTIDE
<222> LOCATION: (1)..(11)

<400> SEQUENCE: 6

Pro Leu Thr Pro Arg His Gly Asp Gly Ser Phe
1               5                   10

<210> SEQ ID NO 7
<211> LENGTH: 12
<212> TYPE: PRT
<213> ORGANISM: Unknown
<220> FEATURE:
<223> OTHER INFORMATION: testing peptide 2
<220> FEATURE:
<221> NAME/KEY: PEPTIDE
<222> LOCATION: (1)..(12)

<400> SEQUENCE: 7

Pro Val Ser Gly Pro Arg His Gly Asp Gly Ser Phe
1               5                   10

<210> SEQ ID NO 8
<211> LENGTH: 13
<212> TYPE: PRT
<213> ORGANISM: Unknown
<220> FEATURE:
<223> OTHER INFORMATION: testing peptide 3
<220> FEATURE:
<221> NAME/KEY: PEPTIDE
<222> LOCATION: (1)..(13)

```
<400> SEQUENCE: 8

Ile Thr Asp Pro Leu Val Pro Arg His Gly Asp Gly Ser
1               5                   10

<210> SEQ ID NO 9
<211> LENGTH: 33
<212> TYPE: PRT
<213> ORGANISM: Unknown
<220> FEATURE:
<223> OTHER INFORMATION: Teduglutide
<220> FEATURE:
<221> NAME/KEY: PEPTIDE
<222> LOCATION: (1)..(33)

<400> SEQUENCE: 9

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 10
<211> LENGTH: 99
<212> TYPE: DNA
<213> ORGANISM: Unknown
<220> FEATURE:
<223> OTHER INFORMATION: Teduglutide
<220> FEATURE:
<221> NAME/KEY: misc_feature
<222> LOCATION: (1)..(99)

<400> SEQUENCE: 10
catggtgatg gtagctttag cgacgaaatg aataccattc tggataatct ggcagcccgt      60
gattttatca attggctgat tcagaccaaa atcaccgac                             99
```